United States Patent
Plietker (10) Patent No.: US 7,485,744 B2
(45) Date of Patent: Feb. 3, 2009

(54) IRON-CATALYZED ALLYLIC ALKYLATION

(75) Inventor: Bernd Plietker, Essen (DE)

(73) Assignee: Universität Dortmund, Dortmund (DE)

( * ) Notice: Subject to any disclaimer, the term of this patent is extended or adjusted under 35 U.S.C. 154(b) by 37 days.

(21) Appl. No.: 11/510,456

(22) Filed: Aug. 25, 2006

(65) Prior Publication Data

US 2007/0049770 A1    Mar. 1, 2007

(30) Foreign Application Priority Data

Aug. 26, 2005    (DE) .................. 10 2005 040 752

(51) Int. Cl.
*C07C 69/34* (2006.01)
(52) U.S. Cl. .................................... 560/190
(58) Field of Classification Search ........................ None
See application file for complete search history.

(56) References Cited

OTHER PUBLICATIONS

Zhou et al. ,J. Org. Chem., 1988, 53, 4421-4422.*
Xu et al., J. Org. Chem., 1987, 52, 974-977.*
Plietker et al., Angewandte Chemie, International Edition (2006), 45(9), 1469-1473.*
Ladoulis, Sandra J. et al., "Iron-Catalyzed 1-19 Allylic Alkylation," Journal of Organometallic Chemistry, Bd. 285, 1985, C13-C16, XP002416506, Tab. 1.
Yamaguchi, H., et al.: "Synthesis of planar chiral η3-allyldicarbonylnitrosyliron complexes and sterochemistry of the complex . . . " In: J. of Organometallic Chemistry, 554,(1998) pp. 167-170.
Silverman, G.S., et al.: "Iron-Promoted Allylic Alkylation: Regiochemical Sterochemical, and Mechanistic Aspects." In: Organometallics, 1986, 5, pp. 2117-2124.
Itoh, K., et al.: "Conjugate addition of allylic groups to a α β-unsaturated carbonyl compounds via . . . " In: J. of Organom. Chemistry, 473, 1994, pp. 215-224.
Davies, S.G., et al.: "The use of [Fe(CO)₃NO] for the carbonylation of primary, secondary and allylic halides." In: J. of Organom. Chemistry, 386, 1990, pp. 195-201.
Eberhardt, Udo, et al.: "Über die stereoselektive Bildung von syn- und anti-Dicarbonyl . . . " In: Chem. Ber., 1988, 121, pp. 1531-1534.
Nakanishi, Saburo, et al.: "Animation of (η3-Allyl) dicarbonylnitrosyliron Complexes . . . " In.: Synthesis, 1998, pp. 1735-1741.
Nakanishi, Saburo, et al.: "A Convenient Synthesis of β,γ-Unsaturated Carboxylic . . . " In: Synthesis, 1994, pp. 609-612.
Zhou, B., et al.: "Studies on the Enantioselectivity in Bu₄N[Fe(CO)₃NO]-Catalyzed Nucleophilic . . . " In: J. Org. Chem., 1988, 53, pp. 4419-4421.
Nakanishi, Saburo, et al.: "Preparation, Ligand Substitution, and Structural Stability of . . . " In: Bull. Chem. Soc. Jpn. 71, 1998, pp. 403-412.
Itoh, K., et al.: "Preparation and Reactivities of (η³-1-and 2-Trimethylsiloxyallyl)Fe(CO)₂NO Complexes . . . " In: Bull. Chem. Soc. Jpn, 64, 1991, pp. 2965-2977.

(Continued)

*Primary Examiner*—Karl J Puttlitz
(74) *Attorney, Agent, or Firm*—Collard & Roe, P.C.

(57) ABSTRACT

A method for performing an iron-catalyzed allylic alkylation includes the preparation of a reaction mixture obtainable from (i) an allylic substrate with the structural element C=C—C—X, wherein X comprises a leaving group that represents a carbonate, (ii) an active Fe(-II) catalyst complex, (iii) at least one ligand, (iv) at least one solvent, and (v) a nucleophile or pronucleophile.

20 Claims, 7 Drawing Sheets

| Item | Solvent[a] | A : B[b] | Conversion [%][c] |
|---|---|---|---|
| 1 | - | Not determined | 8 |
| 2 | Pyridin | Not determined | 6 |
| 3 | PPh₃ | 96 : 4 | 51 |
| 4 | PBu₃ | 92 : 8 | 26 |
| 5 | P(OEt)₃ | Not determined | 12 |
| 6 | dppe | Not determined | 8 |
| 7 | dppp | Not determined | 11 |
| 8 | dppf | Not determined | 13 |

OTHER PUBLICATIONS

Xu, Yuanyao, et a l.: "on the Regio-and Stereoselectivity of . . . " In: J. Org. Chem. 52, 1987, pp. 974-977.

Nakanashi, et al.: CO Insetion of $(\eta^3\text{-allyl})Fe(CO)_2(NO)$ Complexes by Diphosphines In: Organometallics, 15, 1996, pp. 5432-5435.

* cited by examiner

Figure 1

| Item | Solvent[a] | A : B[b] | Conversion [%][c] |
| --- | --- | --- | --- |
| 1 | - | Not determined | 8 |
| 2 | Pyridin | Not determined | 6 |
| 3 | PPh$_3$ | 96 : 4 | 51 |
| 4 | PBu$_3$ | 92 : 8 | 26 |
| 5 | P(OEt)$_3$ | Not determined | 12 |
| 6 | dppe | Not determined | 8 |
| 7 | dppp | Not determined | 11 |
| 8 | dppf | Not determined | 13 |

Figure 2

| Item | Solvent[a] | A : B[b] | Conversion [%][c] |
|---|---|---|---|
| 1 | THF | 96 : 4 | 51 |
| 2 | DME | 92 : 8 | 43 |
| 3 | Acetone | Not determined | 12 |
| 4 | $CH_2Cl_2$ | Not determined | - |
| 5 | Toluene | 97 : 3 | 39 |
| 6 | DMSO | 96 : 4 | 46 |
| 7 | $CH_3CN$ | 58 : 42 | 60 |
| 8 | DMF | 98 : 2 | 95 |
| 9 | NMP | 97 : 3 | 82 |

Figure 3

| Item[a] | Nucleophile | Product | Time [h] | A : B[b] | Yield [%][c] |
|---|---|---|---|---|---|
| 1 | MeO₂C⌒CO₂Me | MeO₂C-CH(CO₂Me)- product | 24 | 98 : 2 | 81 |
| 2 | MeC(O)CH₂CO₂Me | acetyl-CH(CO₂Me)- product | 24 | 96 : 4 | 76 |
| 3 | NC⌒CN | NC-CH(CN)- product | 12 | 97 : 3 | 74 |
| 4 | NC⌒CO₂Me | NC-CH(CO₂Me)- product | 12 | 98 : 2 | 79 |
| 5 | PhO₂S⌒CO₂Me | PhO₂S-CH(CO₂Me)- product | 12 | 97 : 3 | 83 |
| 6 | PhO₂S⌒CN | PhO₂S-CH(CN)- product | 12 | 94 : 6 | 92 |
| 7 | 2-cyanocyclopentanone | quaternary product | 12 | 87 : 13 | 79 |

Figure 4

| Item[a] | Substrate | Product | Time [h] | Yield [%][c] |
|---|---|---|---|---|
| 1 | (prenyl OC(O)OiBu) | MeO₂C-CH(CO₂Me)-CH₂-CH=CMe₂ | 24 | 81 |
| 2 | 1-vinyl-1-(OC(O)OiBu)cyclohexane | 1-vinyl-1-(CH(CO₂Me)₂)cyclohexane | 24 | 76 |
| 3 | CH₂=CH-CH(Me)-OC(O)OiBu | MeO₂C-CH(CO₂Me)-CH(Me)-CH=CH₂ | 24 | 74 |
| 4 | crotyl OC(O)OiBu | MeO₂C-CH(CO₂Me)-CH₂-CH=CH-Me | 24 | 78 |
| 5 | PhCH=CH-CH(Me)-OC(O)OiBu | MeO₂C-CH(CO₂Me)-CH(Me)-CH=CH-Ph | 24 | 81 |
| 6 | PhCH=CH-C*(Me)(OC(O)OiBu)- | MeO₂C-CH(CO₂Me)-C*(Me)-CH=CH-Ph | 24 | 77 |
| 7 | PhCH=CH-CH(OC(O)OiBu)-CH=CH₂ | PhCH=CH-CH(CH(CO₂Me)₂)-CH=CH₂ | 24 | 71 |
| 8 | cyclohexenyl-CH₂-OC(O)OiBu | cyclohexenyl-CH₂-CH(CO₂Me)₂ | 24 | 74 |
| 9 | 2-methylenecyclohexyl-OC(O)OiBu | 2-methylenecyclohexyl-CH(CO₂Me)₂ | 24 | 76 |

IRON-CATALYZED ALLYLIC ALKYLATION

CROSS REFERENCE TO RELATED APPLICATIONS

Applicant claims priority under 35 U.S.C. §119 of German Application No. 10 2005 040 752.8 filed Aug. 26, 2005.

BACKGROUND OF THE INVENTION

1. Field of the Invention

The present invention relates to a method for carrying out an iron-catalyzed allylic alkylation and its use.

2. The Prior Art

In the synthesis of natural products or of pharmacologically interesting compounds, various methods are being developed in synthetic organic chemistry that permit the construction of chiral structures. Numerous methods have been developed to increase activity and selectivity. Among them, for example, are racemate resolution via reversible derivatization with chiral auxiliaries followed by separation, the use of enantiomerically pure starting materials, the use of chiral auxiliaries in stoichiometric reactions, or the use of reactions in the presence of a chiral catalyst.

Among the most important catalytic reactions in organic chemistry for forming carbon-carbon bonds is transition metal-catalyzed allylic alkylation. In this reaction, an allyl complex that reacts with a nucleophile is generated by oxidative addition of a transition metal complex to an allyl substrate. The transition metal is reduced again, and the reaction product is liberated.

However, the preparation of allylically highly substituted carbon structural units represents a central problem of preparative synthetic organic chemistry, because alkylation usually occurs on the less highly substituted carbon. An attack on the sterically favored unsubstituted allyl terminus would lead to the unwanted linear isomer. Therefore, it is of special interest to steer the attack to the more highly substituted allyl end.

Numerous transition metals can be used to cause carbon-nucleophiles to react selectively with allylically activated substrates, wherein the organic parts of the allyl-metal fragments formed can be considered formally as carbocation equivalents. The methods so far known for metal-catalyzed allylic alkylation using palladium, nickel, iridium, rhodium, or similar metals, pass through the formation of intermediate metal-allyl complexes. Among the best-known and most powerful methods developed is asymmetric palladium-catalyzed allylic alkylation by the method of TROST et al. Numerous reviews provide a good survey of its research and application.

Intermediate (π-allyl)metal complexes are formed in transition metal catalysis, that do offer advantages with regard to possible stereoinduction by chiral ligands, but frequently lead to the formation of regioisomeric mixtures in the case of an unsymetrically substituted substrate. Because of this formation, it is often impossible to achieve control of regioselectivity of the alkylation at the differently substituted termini of the allyl fragment.

This frequently undesired side effect can be partially lessened by the use of ligands. Some of the systems do lead to enrichment of the higher branching products that are poorly accessible, but the regioselectivities are unsatisfactory at best.

High regioselectivities play a large role in natural product synthesis (for example, in the synthesis of carbohydrates). Therefore, a need exists for a method for selective allylic alkylations in which the new carbon-carbon bond can be constructed on the carbon that has previously been substituted with the nucleofug.

Furthermore, the catalysts disclosed by the state of the art, most of which contain noble metals, are distinguished by high prices and by their sensitivity to oxygen and water. Such reactions as a rule have to be carried out with strict exclusion of oxygen and water, which from the industrial viewpoint is directly associated with additional costs for equipment. The transition metals used are also toxic, which is particularly troublesome from economic and ecological viewpoints. Workup and disposal of toxic catalysts means additional costs from the necessary safety measures and purification steps.

The development of nontoxic, economical catalysts that are distinguished by a high degree of regioselectivity in allylic alkylation is therefore of great synthetic interest.

Another catalyst that can be used for allylic alkylation is known from the state of the art. As early as 1979, Roustan published the synthesis of an iron complex that catalyzes allylic alkylation. This system was later refined by Zhou by the use of the formal Fe(-II) complex [$Bu_4N$] [$Fe(CO)_3(NO)$] (appeared in 1987). Both catalyst systems are distinguished by a high catalyst load. The allylic alkylation here does not occur with the development of a (π-allyl)metal species.

This Fe(-II) complex was not developed further because of the poor reproducibility of results and the deficient description of the preparation of the active catalyst. The reaction also is carried out there under a toxic CO atmosphere. Handling carbon monoxide is likewise disadvantageous, so that in this case no further scientific research was pursued.

SUMMARY OF THE INVENTION

It is therefore desirable to further develop a method using an Fe(-II) complex for allylic alkylation such that the aforementioned drawbacks are eliminated, and so that large-scale industrial use becomes possible from economic and ecological viewpoints.

To solve this problem the invention, starting from a method of the kind described above, proposes that a reaction mixture obtainable from
  (i) an allylic substrate with the structural element C=C—C—X, wherein X comprises a leaving group that represents a carbonate,
  (ii) an active Fe(-II) catalyst complex,
  (iii) at least one ligand,
  (iv) at least one solvent, and
  (v) a nucleophile or pronucleophile be prepared.

When using carbonates as nucleofuges (leaving groups), an active base is generated in situ that is used for the deprotonation of the pronucleophile. The use of a carbonate as the leaving group according to the invention allows a salt-free reaction method, which makes great sense for uses on the preparative scale.

It is preferred for the carbonate to have the structural element OC(O)OR, wherein R represents unbranched or branched, substituted or unsubstituted hydrocarbon; in particular, alkyl groups such as methyl, ethyl, propyl, butyl, and/or aryl groups are useful, for example. R is preferably an isobutyl group. This circumstance is of especially great importance for industrial applications, because the byproducts of the reaction, namely $CO_2$ and an alcohol R—OH, are nontoxic and are readily removed.

The Fe(-II) catalyst complex has the advantage that it is less costly than any noble metal catalysts known from the state of the art.

The iron catalyst complex used is of the type [Cation] [Fe(CO)$_3$(NO)], preferably of the type [R$_4$N] [Fe(CO$_3$(NO)], and very preferably the Zhou metal complex [Bu$_4$N] [Fe (CO)$_3$(NO)]. This complex can be stored for a long time and is easy to use. Any cations can be used.

The iron catalyst complex can be prepared only in very poor yields by the method of Xu and Zhou, *J. Org. Chem.* 1987, 52, 974-97. The improved method of Yoshio Otusji from *Bull. Chem. Soc. Jpn.* 1991, 64, 2965-2977, starting from Fe(CO)$_3$, provides higher yields. However, the activity of the iron catalyst is unsatisfactory at best.

In departure from the method in the literature, by which the iron catalyst complex is obtainable only in the form of a catalytically inactive oily crude product, recrystallization from methanol and water is preferably used to work-up the iron catalyst complex according to the invention. This improved method for preparing a catalytically active iron catalyst complex is described in further detail in the Example. Using this optimized method, the iron catalyst complex is obtained in the form of a yellow solid that has the activity and purity of at least 80% necessary for the reaction. The iron catalyst complex is stable to air and water; it can be prepared in large amounts and stored for a long time with no loss of activity.

Tertiary phosphines as transition metal ligands are known from the state of the art based on numerous specific properties. They are distinguished by the ability to stabilize low oxidation states of the metal center. The metal centers in the transition metal-phosphine complexes are mostly present in discrete molecular form. These compounds are often soluble in organic solvents over a wide range. Varying the substituents in PR$_3$ permits the electronic and steric properties of the ligand to be adjusted, and with them those of the metal center also.

Monodentate ligands are preferably used, and basic phosphines are particularly preferred. They increase reactivity and can increase the longevity of the catalyst.

It is especially preferred to derivatize the catalyst in situ by adding triphenylphosphine as ligand. The catalyst has substantially greater stability from the addition of phosphine, so that it is not necessary to use a toxic CO atmosphere.

It can be shown that a new active iron catalyst complex is formed with the phosphine during the alkylation that can be isolated and characterized. This new catalyst can be used for many areas of application.

Another point that is often undervalued is the choice of solvent. It has been found that strongly coordinating solvents like N,N-dimethylformamide (DMF) permit a further increase of reactivity. Other possible solvents are given in the Examples (FIG. 2), such as dimethoxyethane (DME), dimethylsulfoxide (DMSO), and N-methylpyrrolidone (NMP).

Another advantage over the state of the art is the reduction of the necessary amount of catalyst from 25 mol-% to 2.5 mol-%.

The iron-catalyzed allylic alkylation can be used on a number of different carbon nucleophiles or pronucleophiles. These compounds are preferably CH-acids. Nucleophiles or pronucleophiles containing nitrile proved to be especially reactive. The reaction time is shortened by a factor of 2 in their presence.

N-, O-, and S-nucleophiles or pronucleophiles can also be used to advantage.

The iron-catalyzed allylic alkylation according to the invention therefore represents a simple and new method for selective carbon-carbon bond formation starting with allyl carbonates. Alkylation occurs exclusively on the carbon of the allyl fragment that was previously substituted with the leaving group, the carbonate.

Another aspect of the invention is the use of the method according to the invention for the synthesis of natural products, active substances, and unnatural amino acids. Use in asymmetric olefinization is also practical.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings.

DETAILED DESCRIPTION OF PREFERRED EMBODIMENTS

Figure 1:
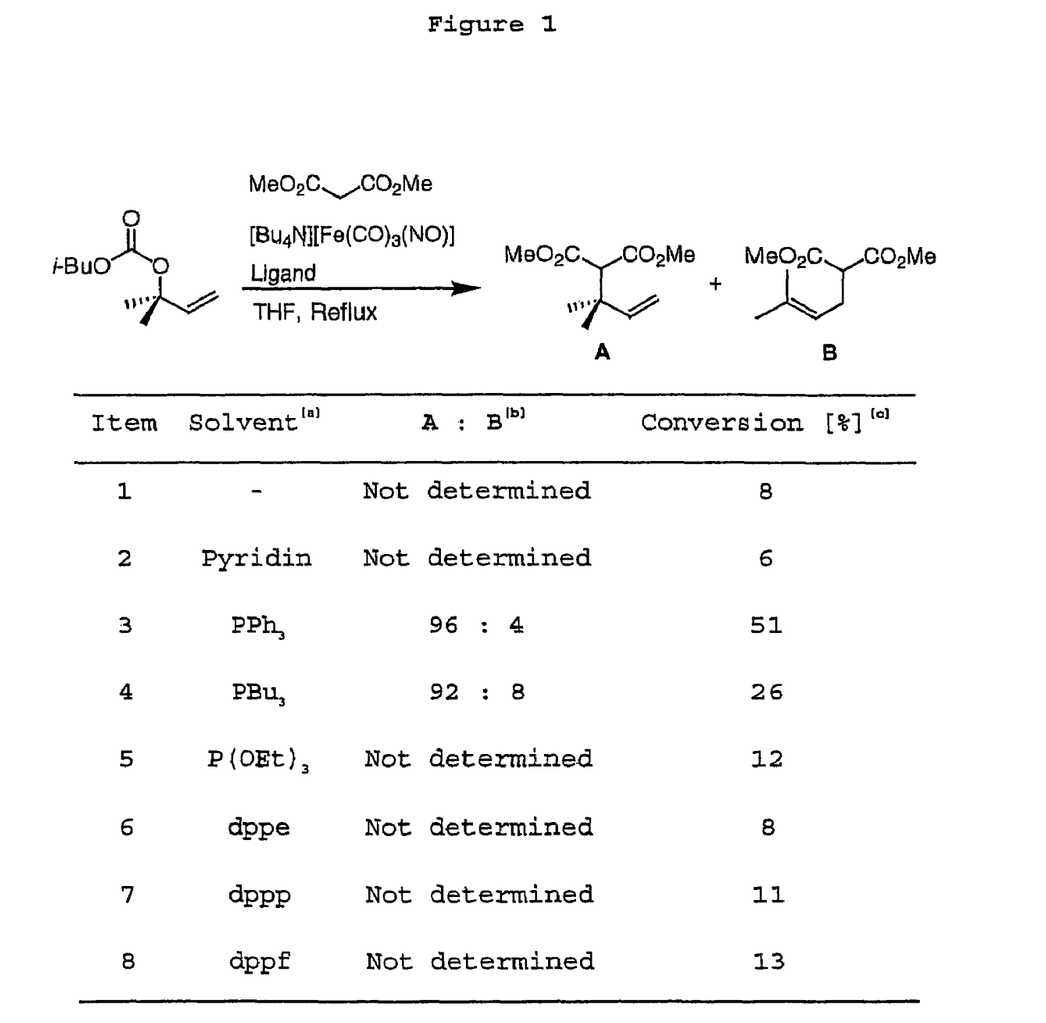
FIG. 1 shows ligand effect in allylic alkylation.

Turning now in detail to the drawings, FIG. 1 represents a reaction equation. Numerous ligands are listed in the attached table. PPh$_3$ and PBu$_3$ show greater regioselectivity than the other ligands, such as diphenylphosphinoethane (dppe), diphenylphosphinopropane (dppe), and diphenylphosphinoferrocene (dppf).

[a] all of the reactions were carried out on a 1-mmole scale in the presence of 10 mol-% Fe catalyst, 10 mol-% ligand, and 2 equivalents of the nucleophile in 5 ml of absolute tetrahydrofuran (THF), and were terminated after 24 h; [b] Determination was by gas chromatography (GC); [c] Determination via GC relative to undecane as the internal standard.

Figure 2:
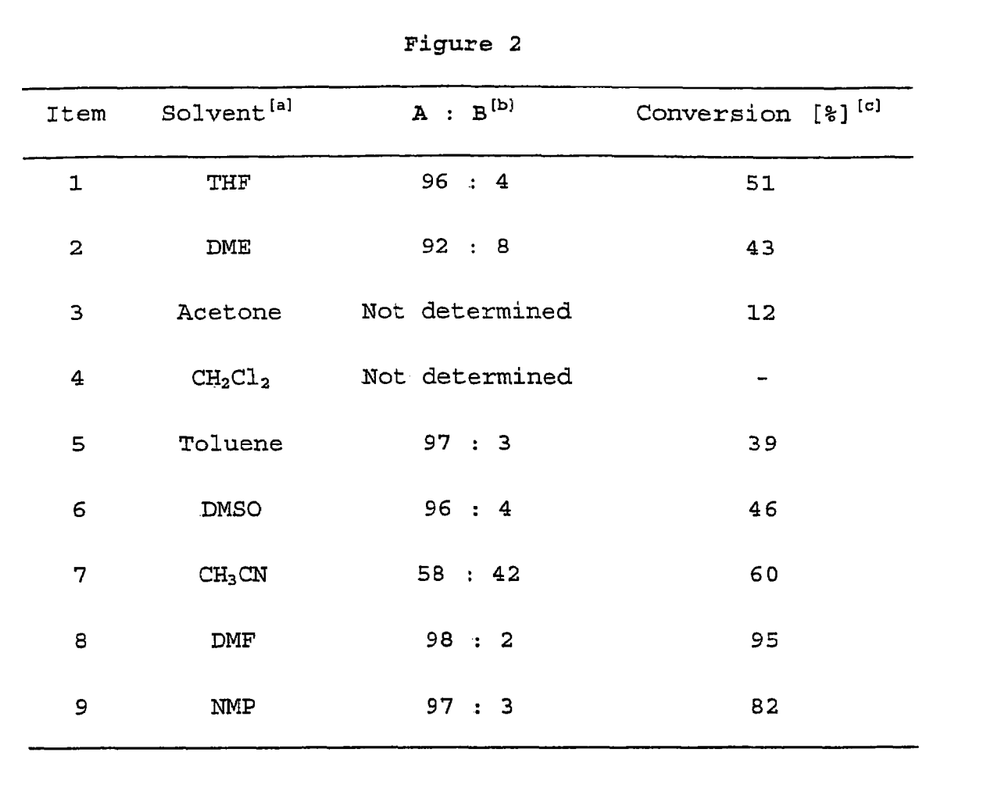
FIG. 2 shows solvent effect in allylic alkylation.

FIG. 2 shows [a] all reactions that were carried out in the presence of 10 mol-% PPh$_3$ under the conditions described in FIG. 1; [b] Determined via GC; [c] Determined via GC relative to undecane as the internal standard.

No great regioselectivity was found when using acetonitrile. This result indicates an alternative allyl-metal mechanism.

Figure 3:
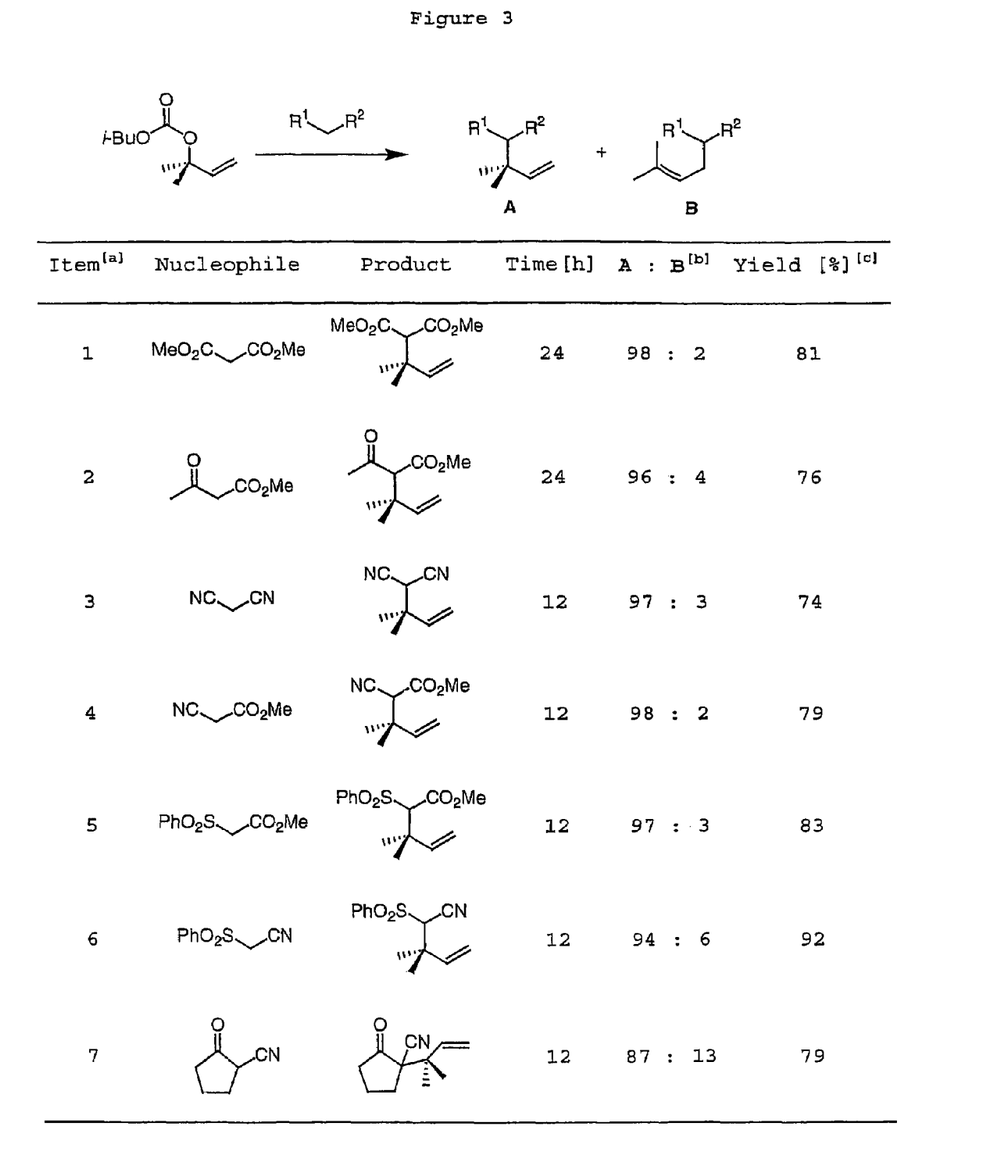
FIG. 3 shows allylic alkylation of different nucleophiles.

FIG. 3 shows a reaction equation of allylic alkylation and a table of possible nucleophiles. The bandwidths of R$^1$ and R$^2$ are almost limitless.

[a] All of the reactions were carried out on a 1-mmol scale in the presence of 2.5 mol-% Fe catalyst, 3 mol-% PPh$_3$, and 2 equivalents of the nucleophile in 1 ml of absolute N,N-dimethylformamide (DMF); [b] Determined via GC; [c] Determined via GC relative to undecane as the internal standard.

Figure 4:
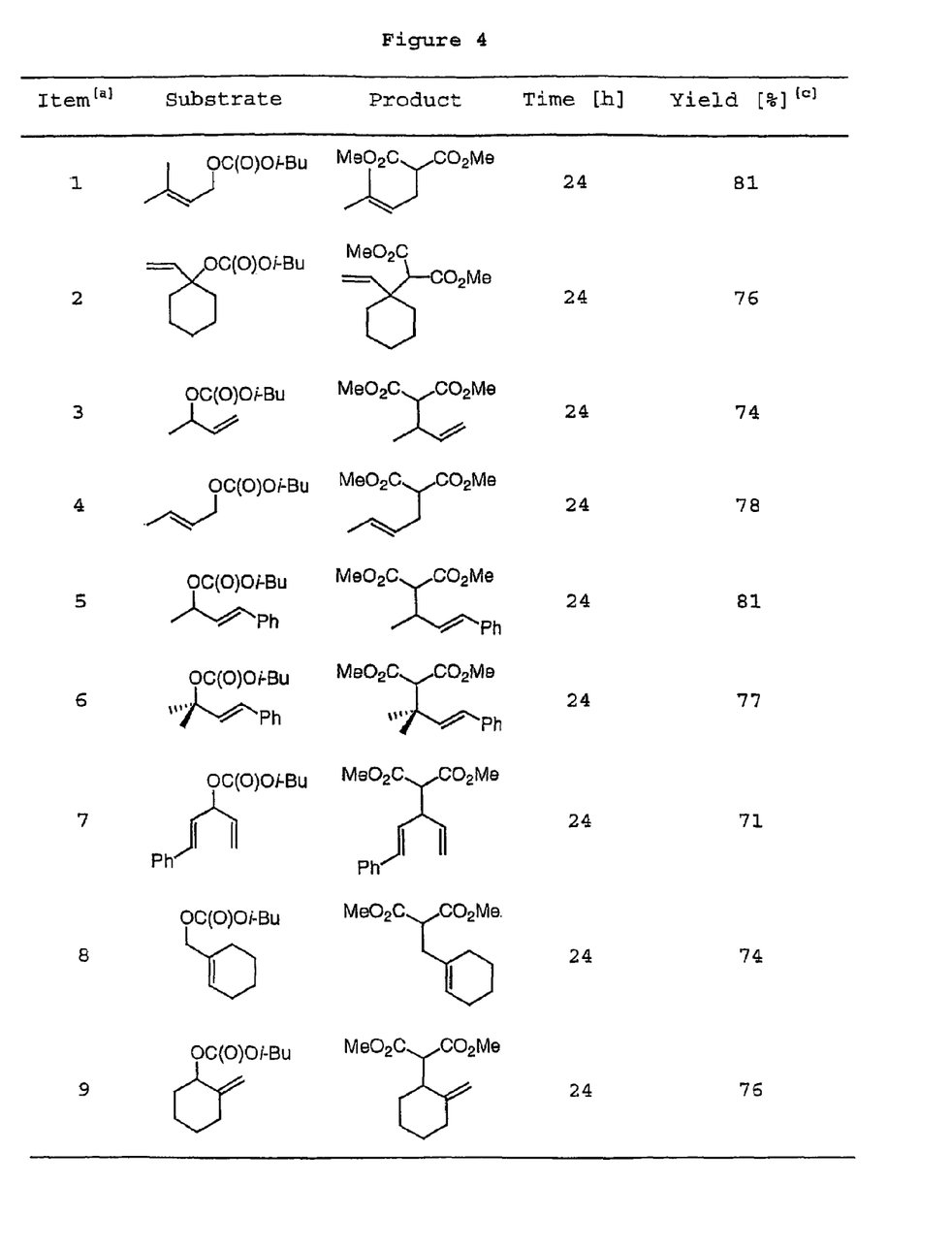
FIG. 4 shows allylic alkylation of different substrates.

FIG. 4 shows a table of possible substrates.

[a] All of the reactions were carried out on a 1-mmol scale in the presence of 2.5 mol-% Fe catalyst, 3 mol-% PPh$_3$, and 2 equivalents of the nucleophile in 1 ml of absolute DMF; [b] Determined via GC; [c] Determined via GC relative to undecane as the internal standard.

A further increase of reactivity was achieved by increasing the substrate concentration from 0.2 mol/l originally to 1 mol/l, and associated with this was a reduction of catalyst concentration to 2.5 mol-% with the same regioselectivity or higher.

Figure 5:
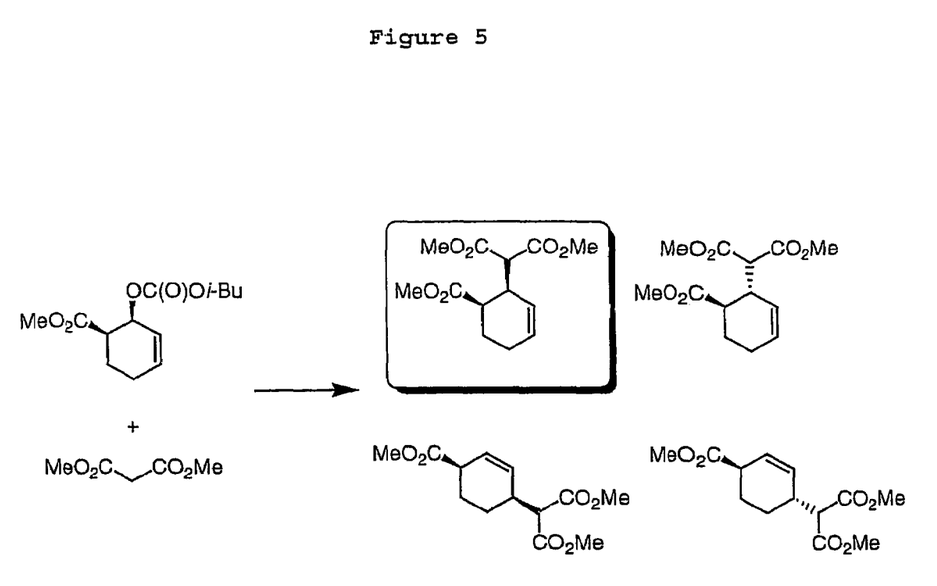
FIG. 5 shows regioselectivity and stereoselectivity of iron-catalyzed allylic alkylations.

FIG. 5 shows the regioselectivity of the alkylation according to the invention. This regioselectivity suggests the conclusion that this reaction is different from most of the current allylic alkylations in that no ($\eta^3$-allyl)-intermediate is involved. Only a highly stereoselective double $S_N2'$ anti-addition of both the metal in the first step and the nucleophile in the second step makes possible the observed high regio- and stereoselectivity.

Figure 6:
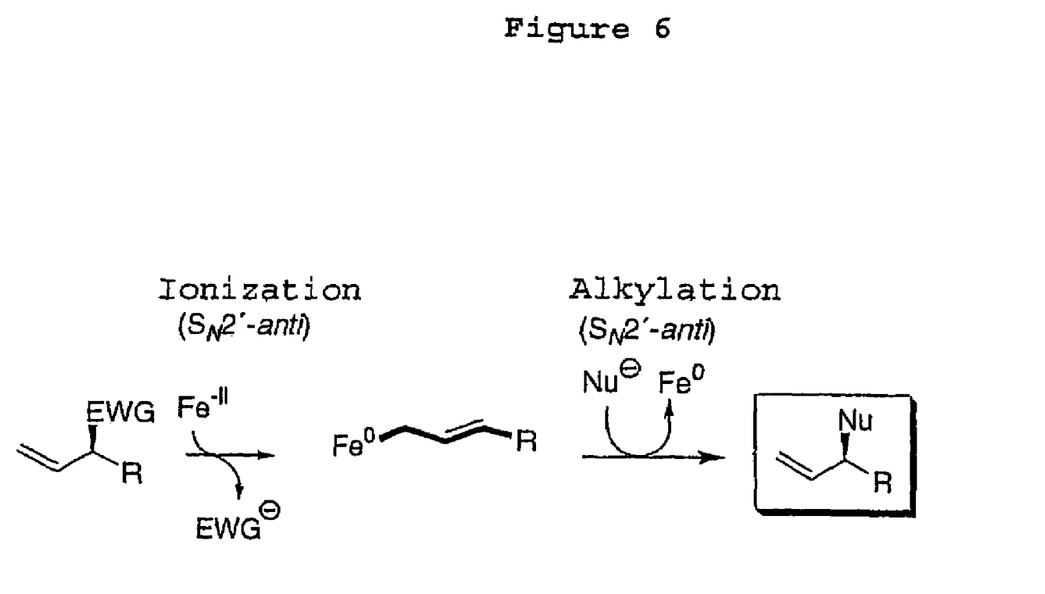
FIG. 6 shows preservation of regio- and stereoselectivity in the ($\eta^1$-allyl) mechanism.

FIG. 6 shows a possible double $S_N2'$ anti-addition diagram.

Figure 7:
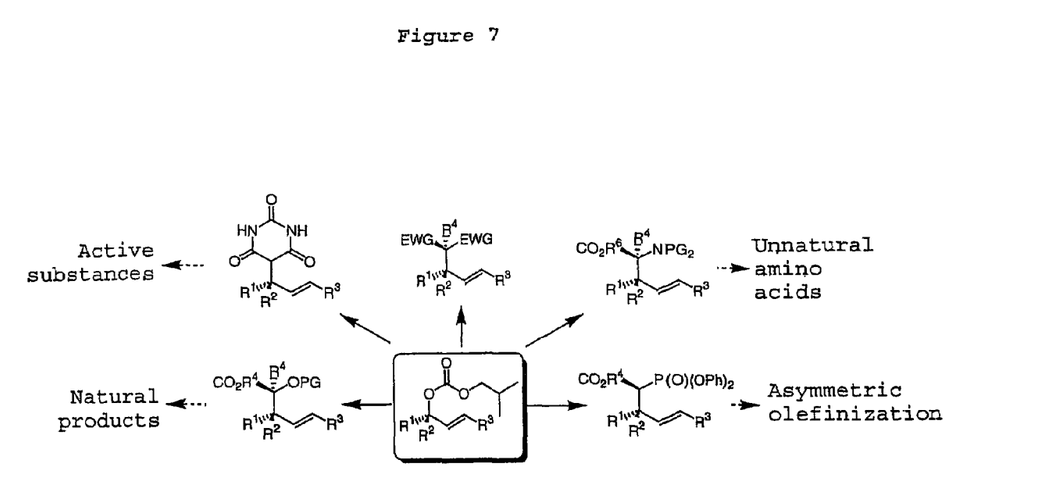
FIG. 7 shows allylic alkylation as a key process in organic chemistry.

FIG. 7 shows some examples of the use of the alkylation according to the invention.

EXAMPLE 1

Preparation of dimethyl 2-(1',1'-dimethylallyl)malonate

The iron catalyst (10.2 mg, 0.025 mmol, 2.5 mol-%) and PPh$_3$ (6.9 mg, 0.03 mmol, 3 mol-%) are placed in a 10-ml Schlenk tube in dry DMF (1 ml) under argon. The allyl carbonate (186 ml, 1 mmol) and dimethyl malonate (232 mg, 2 mmol) are added. The mixture is then heated at 80° C. for 24 h in the sealed Schlenk tube. After cooling to room temperature, the mixture is diluted with diethyl ether (20 ml), and then washed successively with water (10 ml), 2 N NaOH solution (10 ml), and water (10 ml). The combined organic phases are then dried over a 1:1 mixture of Na$_2$SO$_4$ and activated charcoal (about 5 g). After filtration and evaporation, a light yellow liquid is obtained, which is purified by column chromatography (isohexane/diethyl ether, 5:1). Yield: 162 mg (0.81 mmol, 81%).

EXAMPLE 2

Preparation of the active iron catalyst complex [Bu$_4$N] [Fe(CO)$_3$(NO)]

A solution of Fe(CO)$_5$ (11.8 g, 60 mmol) in degassed CH$_2$Cl$_2$ (20 ml) is added to a solution of NaNO$_2$ (4.2 g, 60 mmol) and tetra(n-butyl)ammonium bromide (19 g, 60 mmol) in degassed water (20 ml) under argon at room temperature. The mixture is stirred for four hours at this temperature. The organic phase is separated and washed twice with water (20 ml). The solvent of the organic phase is removed without drying over Na$_2$SO$_4$ under vacuum with a bath temperature of 30° C. The oily, dark brown residue is taken up in methanol (20 ml) and is again concentrated under vacuum. This procedure is repeated until the distillate is colorless. A little methanol is then added to the brown crude product and water (200 ml) is added to it with vigorous stirring. After about 30 min, the catalyst separates out in the form of a yellow solid. It can then be filtered off in air. To dry it, the solid is taken up in a little absolute CH$_2$Cl$_2$ and residual water still present is removed by azeotropic distillation under vacuum. The deep yellow solid is dried under high vacuum and can be used directly in catalysis with no further purification steps. The complex can be stored under argon for weeks at −20° C. with no loss of activity. Yield: 22.7 g (55.2 mmol, 92%).

Although only few embodiments of the present invention have been shown and described, it is to be understood that many changes and modifications may be made thereunto without departing from the spirit and scope of the invention as defined in the appended claims.

What is claimed is:

1. A method for performing an iron-catalyzed allylic alkylation comprising (a) preparation of a salt-free reaction mixture obtainable from
    (i) an allylic substrate with a structural element C=C—C—X, wherein X comprises a leaving group that represents a carbonate,
    (ii) an active Fe(-II) catalyst complex,
    (iii) at least one ligand,
    (iv) at least one solvent, and
    (v) a nucleophile or pronucleophile; and
(b) carrying out an iron-catalyzed allylic alkylation in the absence of carbon monoxide (CO) using the reaction mixture to selectively form carbon-carbon bonds on the allylic substrate with the nucleophile or pronucleophile.

2. The method according to claim 1, wherein the carbonate has a structural element OC(O)OR, wherein R has an unbranched or branched group, and is substituted or unsubstituted.

3. The method according to claim 2, wherein R is an alkylgroup or an aryl group.

4. The method according to claim 3, wherein R is an isobutyl group.

5. The method according to claim 1, wherein the at least one ligand is a phosphine.

6. The method according to claim 5 wherein the at least one phosphine is a basic phosphine.

7. The method according to claim 5 wherein the at least one phopspine is a tertiary phospine.

8. The method according to claim 1, wherein the nucleophile or pronucleophile is a carbon nucleophile.

9. The method according to claim 8, wherein the carbon nucleophile is a CH acid nucleophile or pronucleophile.

10. The method according to claim 1, wherein the nucleophile is an N-, O-, or S-nucleophile.

11. The method according to claim 1, wherein the solvent is N,N dimethylformamide, tethrahydrofuran, or N-methylpyrrolidone.

12. The method according to claim 1, wherein the Fe(-II) catalyst complex has a purity of at least 80%.

13. The method according to claim 12, wherein the Fe(-II) catalyst complex is [Bu$_4$N] [Fe(CO)$_3$ (NO)] and less than 25 mol-% of the catalyst complex [Bu$_4$N] [Fe(CO)$_3$ (NO)] is used.

14. The method according to claim 1, wherein the Fe(-II) catalyst complex is worked up by recrystallization.

15. The method according to claim 14 wherein the Fe(-II) catalyst complex is worked up by recrystallization from methanol and water.

16. A method of synthesizing a product comprising:
    (a) preparation of a salt-free reaction mixture obtainable from
        (i) an allylic substrate with a structural element C=C—C—X, wherein X comprises a leaving group that represents a carbonate,
        (ii) an active Fe (-II) catalyst complex,
        (iii) at least one ligand,
        (iv) at least one solvent, and
        (v) a nucleophile or pronucleophile with the nucleophile or pronucleophile; and
    (b) carrying out an iron-catalyzed allylic alkylation in the absence of carbon monoxide (CO) using the reaction mixture to selectively form carbon-carbon bonds on the allylic substrate to synthesize a product wherein the product is a natural product.

17. The method according to claim 1, wherein the iron-catalyzed allylic alkylation is used to synthesize an active substance.

18. The method according to claim 1, wherein the iron-catalyzed allylic alkylation is used to synthesize an unnatural amino acids.

19. The method according to claim 1, wherein the iron-catalyzed allylic alkylation is used for asymmetric olefinization.

20. The method according to claim 1, wherein [Bu$_4$N][Fe(CO)$_3$(NO)] is used to carry out the method.

* * * * *